United States Statutory Invention Registration [19]

[11] Reg. Number: H600

Tanaka et al.

[43] Published: Mar. 7, 1989

[54] WHOLE BLOOD ANALYTICAL ELEMENT AND METHOD OF ANALYZING WHOLE BLOOD USING THE SAME

[75] Inventors: Mitzutoshi Tanaka; Shigeru Nagatomo; Harumi Katsuyama; Kazuya Kawasaki, all of Saitama, Japan

[73] Assignee: Fuji Photo Film Co., Ltd., Kanagawa, Japan

[21] Appl. No.: 171,326

[22] Filed: Mar. 21, 1988

[30] Foreign Application Priority Data

Mar. 20, 1987 [JP] Japan ..... 62-67511
Apr. 8, 1987 [JP] Japan ..... 62-86095

[51] Int. Cl.[4] ..... G01N 33/49
[52] U.S. Cl. ..... 422/56; 422/57; 422/58; 436/170

*Primary Examiner*—John F. Terapane
*Assistant Examiner*—Susan Wolffe
*Attorney, Agent, or Firm*—Sughrue, Mion, Zinn, Macpeak & Seas

[57] ABSTRACT

A multilayer analytical element for determining an assay of a component in whole blood sample is disclosed, which comprises at least two water-permeable layers, wherein one layer is a sample spreading layer and the other layer is a reagent layer, wherein one layer or more of said water-permeable layers contain a composition which interacts with said component in whole blood sample, wherein the composition forms a dye capable of being detected by a spectrophotometry at a wavelength of 600 n.m. or longer, when the composition interacts with said component in whole blood sample.

8 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

WHOLE BLOOD ANALYTICAL ELEMENT AND METHOD OF ANALYZING WHOLE BLOOD USING THE SAME

FIELD OF THE INVENTION

This invention relates to a multilayer analytical element for whole blood and also a method of analyzing specific components in whole blood using the analytical element.

BACKGROUND OF THE INVENTION

In order to perform health management for prophylaxis and treatment, it is frequently required to determine the presence of various components in the blood of the patient. For example, the level of glucose or cholesterol in the blood is important for effective prophylaxis of various diseases such as diabetes, hypoglycemia, liver trouble, thyroid trouble, atherosclerosis, etc.

Hitherto, these components in the blood have been determined in the serum or plasma after removing the red blood corpuscles from the blood. However, in order to avoid this troublesome operation and the increase in cost for the equipment required to separate the red blood corpuscles from the other components of the blood, it is preferred that the components being analyzed in the whole blood can be determined without separating the red blood corpuscles. Also, if undiluted whole blood can be used for the analysis, samples can be more simply and quickly obtained and assayed. This is particularly important for the health management in a home or a practitioner's office, etc., wherein the analysis is required to be as simple as possible.

A dry chemical analysis is known (i.e., clinical analysis using an analytical element in a substantially dry state, such as a test piece or a multilayer analytical element, containing therein anlytical reagent(s)). Dry chemical analysis is excellent as compared to wet chemical analysis (i.e., a method using analytical reagent(s) dissolved in a solution) in terms of easiness of use, economy, and quickness of analysis. However, in the case of analyzing whole blood using conventional dry chemical analysis, it is required to first remove the blood corpuscles (red blood corpuscles and white blood corpuscles) and other unnecessary high molecular components from the sample or to separate these unnecessary components from the sample within the analytical element by some means.

In such an analysis, the necessity of isolating the serum or plasma from the blood corpuscles in the whole blood must be avoided because the operation of removing the blood corpuscles from the serum or plasma using a filter element requires a very long time and much trouble. In addition, part of the serum or plasma is inevitably lost in the filter element when such an assay component passes through the filter element, which possibly makes the analysis incorrect.

Some conventional dry analytical elements require removing the blood corpuscle components by, after permeating the serum or plasma into the analytical element, wiping off the blood corpuscle components. The analysis of whole blood is possible by using a multilayer analytical element having a porous layer which catches the blood corpuscle components occupying a large portion of the whole blood whereby the serum or plasma can pass through into a reagent layer containing a reagent causing a detectable change in the presence of a specific component.

U.S. Pat. No. 4,042,335 describes whole blood analysis using a multilayer analytical element. The multilayer analytical element described therein is composed of a support having formed thereon, in succession, a recording layer, a light blocking layer, and a reagent layer. The reagent layer can also function as a porous spreading layer and the light blocking layer can also function as a barrier an impermeable layer capable of removing the whole blood corpuscles so as to prevent the corpuscles from reaching the recording layer, whereby disturbances caused by hemoglobin can be avoided (see, FIG. 1 of the aforesaid U.S. Patent).

The aforesaid analytical element can measure assay materials in whole blood, however, has various problems. First, a detectable material which can quickly diffuse through the corpuscle impermeable layer into the recording layer and has a sufficiently high extinction must be used. However, only a few of detectable material (dyes, coloring agents, etc.) can simultaneously satisfy the aforesaid requirements.

Second, in the case of separating corpuscle components within the analytical element, the porosity or the size of pores of the surface with which the blood sample is brought into contact must be sufficiently large to completely absorb the sample. However, if the pore structure is too rough, the analysis element is mechanically unstable, i.e., is liable to be broken.

SUMMARY OF THE INVENTION

The object of this invention is, therefore, to provide a dry analytical element for quickly determining assay components in whole blood sample.

Another object of this invention is to provide an analytical method using the analytical element.

The dry system multilayer analytical element of this invention for quantitative assay of a component in whole blood sample comprises at least two water-permeable layers, wherein one layer is a sample spreading layer and the other layer is a reagent layer, wherein one layer or more of said water-permeable layers contain a composition which interacts with said component in whole blood sample, wherein the composition forms a dye capable of being detected by a spectrophotometry at a wavelength of 600 n.m. or longer, when the composition interacts with said component in whole blood sample.

A preferred embodiment of this invention is a multilayer analytical element wherein one of the aforesaid water-permeable layers is a liquid spreading layer, the other is a reagent layer containing at least a component capable of forming the aforesaid dye, and a corpuscle filter layer is disposed between the aforesaid liquid spreading layer and the reagent layer or the aforesaid liquid spreading layer may also function as a corpuscle filter layer, or further a light reflection layer may be disposed between the aforesaid liquid spreading layer and the reagent layer. If desired, the entire interacting composition described above may exist in the reagent layer.

The analytical method of this invention is a method of determining or detecting an assay component in whole blood comprising the steps of:

(A) contacting a whole blood sample with the aforesaid analytical element to form dye capable of being detected by a spectrophotometer at a wavelength of 600 n.m. or longer and (B) detecting the dye at a wavelength of 600 n.m. or longer.

DETAILED DESCRIPTION OF THE INVENTION

The analytical element and the analytical method of this invention can overcome the aforesaid problems in conventional whole blood analysis. That is, according to this invention, the analysis can be carried out easily, quickly, and accurately and also an undiluted whole blood sample can be analyzed. Further, in this invention, it is unnecessary to first separate the serum or plasma from the other cell components of the blood (i.e., whole blood). In addition, in this invention, it is unnecessary to wipe off excessive blood (i.e., corpuscle components) and dilute the blood sample.

Since the dye formed by the interaction with the assay component is detected by a spectrophotometer at a wavelength of 600 n.m. or longer, the disturbances caused by hemoglobin can be avoided.

The analytical method of this invention is very quick. That is, the analysis can be usually finished within several minutes or, in some cases, within 2 minutes. Further, the analysis of this invention is relatively barely influenced by the variation of the hematocrit value in the blood.

This invention is useful for the determination of metabolites such as glucose, cholesterol, uric acid, glycerol, triglyceride, bilirubin, etc., as well as is also useful for the measurement of enzyme activity of dehydrase, creatine kinase, trans aminase (e.g., alanineaminotransferase, asparagineaminotransferase, etc.), hydrolase (e.g., emylase acid phosphatase, and alkali phosphatase, etc.), etc.

The invention can be also used for an immunity analysis using a specific antibody or antigen.

The analytical method of this invention can be applied to the analysis of diluted or undiluted whole blood sample but one of the advantages of this invention is that undiluted whole blood sample can be analyzed as it is. Undiluted whole blood sample means whole blood without being diluted with a physiological saline solution, serum, plasma, etc.

This invention is attained by a dry system multilayer analytical element having at least two water permeable layers having each different functions, that is (1) a liquid spreading layer which can receive or absorb a whole blood sample (of, e.g., 1 to 20 $\mu$l) and does not need the wiping off of excessive blood and (2) a coloring layer (reagent layer) for forming a dye by causing a reaction with an assay component. Each of the two layers may be composed of two or more layers. Also, the analysis element may further have a light-reflection layer or a corpuscle filter layer as described in U.S. Pat. No. 4,042,335.

The liquid spreading layer is composed of a fibrous or non-fibrous material having a proper porosity and mean pore size capable of absorbing whole blood or a mixture of these materials as is disclosed in U.S. Pat. Nos. 3,992,158 and 4,292,272. It is preferred that the liquid spreading layer provides whole blood of uniform concentration per unit area to the surface of another water-permeable layer adjacent to the liquid spreading layer in liquid contact relation.

The useful liquid spreading layer is composed of a cloth described in U.S. Pat. No. 4,292,272 and a fibrous material such as a knitting described in Japanese patent application (OPI) No. 222769/85. (The term "OPI" as used herein indicates an "unexamined published application") Also, the liquid spreading layer may be composed of a non-fibrous isotropic porous material (e.g., a brush polymer) described in U.S. Pat. No. 3,992,158.

It is, however, preferred that the liquid spreading layer of this invention also functions to filter off substantially all of or at least a part of the corpuscles. The aforesaid cloth or knitting is useful for this purpose.

The liquid spreading layer in this invention may contain a hydrophilic polymer or a surface active agent as described in Japanese patent application (OPI) No. 222770/85, Japanese patent application Nos. 122875, 122876, and 143754/86, for controlling the liquid spreading area, the spreading speed, etc.

The reagent layer of the dry analytical element according to the present invention may comprise a reagent which produces detectable component, such as a substance forming or changing color, fluorescent substance, etc. by a reaction with a substance to be determined and may contain, if necessary, a hydrophilic polymer, a buffer agent, light-shielding fine particles (either reflective or absorbable), and the like.

The hydrophilic polymer which can be used in the reagent layer includes starch, cellulose, agarose, gelatin and derivatives thereof (e.g., hydroxymethylated derivatives, hydroxypropylated derivatives, etc.), acrylamide polymers, copolymers of acrylamide and various vinyl monomers, polyvinyl alcohol, copolymers of vinylpyrrolidone and various vinyl monomers, acrylate polymers, copolymers of acrylates and various vinyl monomers, and the like. Of these hydrophilic polymers, polyvinyl alcohol, vinylpyrrolidone polymers, acrylamide polymers and cellulose derivatives are preferred.

The reagent layer and/or the liquid spreading layer of the analytical element of this invention contains at least one kind of an interacting composition. The composition contains at least one active component which causes an interaction with an assay component in whole blood sample or the reaction product or hydrolysis product of the assay component when a whole blood sample containing the assay component is brought into contact with the liquid spreading layer or the reagent layer.

The feature of the analytical element or the analytical method of this invention is that a dye capable of being detected by a spectrophotometer at a wavelength of 600 n.m. or longer is formed directly or indirectly by the aforesaid interaction. Such a dye must have a sufficiently high absorbance that the significant optical density thereof can be observed at a wavelength of 600 n.m. or longer. The dye may be formed by the interaction of a desired assay component in the blood and the dye forming material or may be formed by the liberation of a diffusible dye from a non-diffusible dye.

The term "interaction" indicates a chemically active interaction, a catalytically active interaction as in the formation of an enzyme-base composite, an ommunoactive interaction as in an antibody-antigen reaction, or all other chemical or physical interactions capable of liberating or forming a detectable dye, the density of which directly or indirectly shows the existence or the concentration of a specific assay component.

The aforesaid interacting composition is determined by the analysis reaction employed. A useful interacting composition contains, for example, a material having a dehydrogenase activity. A dehydrogenase active material such as glycerol dehydrogenase, cholesterol dehydrogenase, etc., can be incorporated in the reagent layer or the liquid spreading layer of the analytical element for analyzing a component which is the substrate of such an enzyme.

Other example of the interacting composition is a material having an oxydase activity. An oxydase active material such as glucose oxydase, cholesterol oxydase activity, pyrubic acid oxydase, etc., can be incorporated in the reagent layer or the liquid spreading layer of the analytical element for analyzing a component which is the substrate of the enzyme.

It is preferred that the interacting composition contains a dye-forming composition. In the analytical element of this invention, a composition for forming a dye by the oxidation of a leuco dye is useful. Examples of such a leuco dye are triarylmethaneleuco dyes, as described in U.S. Pat. No. 4,089,747, Japanese patent application (OPI) No. 193352/84, triarylimidazole leuco dyes, etc., and so on.

The dye-forming composition may contain a compound forming a dye in the molecule when oxidized or by a coupling reaction with the reduced product thereof. For example, there are various compounds having a hydroxy group, such as o-aminophenols, 4-alkoxynaphthols, 4-amino-5-pyrazolones, cresols, pyrogallols, guaiacol, oxynol, catechol, fluoroglycinol, p-dihydroxydiphenylgallic acid, pyrocatechin, and salicylic acid. These compounds are described in Mees and James, *The Theory of the Photoqraphic Process,* 3rd edition (1966), in particular Chapter 17.

In other embodiment, the dye may be formed by a dye-forming composition containing a condensation product of an oxidizable compound and a coloring agent. Examples of the oxidizable compound are bensidine and homologs thereof, p-phenylenediamines, p-aminophenols, aminoantipyrine (e.g., 4-aminoantipyrine), etc. Also, coloring agents including various kinds of self-coupling compounds are described in Kosar, *Liqht-Sensitive Systems,* pages 215–249 (1965).

As coloring agents useful for analysis forming hydrogen peroxide in the system, there are toluidines as described in U.S. Pat. Nos. 4,251,629, 4,260,679, and 4,396,714, Japanese patent publication No. 22200/83, European patent application No. 68,356, British patent application No. 2,107,863, Japanese patent application (OPI) No. 898/83, etc.

Examples of useful toluidine compounds are N-ethyl-N-2-sulfoethyl-m-toluidine, N-ethyl-N-2-carboxyethyl-m-toluidine, N-2-carboxyethyl-m-toluidine, N-sulfomethyl-p-toluidine, and N-methyl-N-(2,3-dihydroxypropyl)-m-toluidine.

As other useful coloring agents, there are dihydroindoles, tetrahydroxyquinolines, 1,7-dihydroxyanphthalenes, substituted aniline compounds (e.g., 8-aniline-1-naphthalene-sulfonic acid and N-methyl-N-sulfopropylaniline), 7-dihydroxynaphthalene, etc.

The dye-forming composition may be composed of a compound capable of forming a dye in the presence of a reduction type coenzyme and an electron transferring agent.

The dye may be a dye diffusible and capable of being transferred from the reagent layer into a detection layer containing no reagent or may be a non-diffusible dye. A non-diffusible dye has, for example, a so-called ballast group in the molecule thereof. Also, a compound composed of an oligosaccharide bonded thereto a substituent capable of forming a dye molecule can be utilized as such a non-diffusible dye.

The detection layer is a layer which is substantially permeable to a substance to be finally detected and contains no reagent. This layer comprises a hydrophilic polymer as a main component and, if desired, a surface active agent (cationic, amphoteric or nonionic), a hardener, a buffer agent, etc.

The hydrophilic polymer which can be used for the detecting layer is a natural or synthetic hydrophilic polymer usually having a degree of swelling of from about 1.5 to about 20, and preferably, from about 2.5 to about 15, when it absorbs water.

All amount of the reagent composition (interacting composition) may be contained in the reagent layer. In the other embodiment, a component of the reagent composition may be contained in the reagent layer and the remainder is contained in the liquid spreading layer. For instance, a composition producing an intermediate compound by a reaction of an assay and a reagent may be contained in the liquid spreading layer and a composition (an indicator) producing a dye by an reaction with the intermediate compound may be contained in the reagent layer. Between the reagent layer and the liquid spreading layer, gas-transmissible layer, interferring substance-eliminating layer, etc., as is disclosed in U.S. Pat. No. 4,066,403 may be set, and further these layers may be water-impermeable layer, if required The reagent layer may be composed of a fibrous porous material such as a filter paper a non-woven fabric etc., or a non-fibrous porous material. The reagent layer preferably comprises cellulose esters as is disclosed in Japanese patent publication No. 21677/83, U.S. Pat. No. 1,421,341, etc., and more preferably comprises a brush polymer such as cellulose acetate, cellulose acetate/cellulose butyrate, cellulose nitrate, etc. In addition, the reagent layer may be composed of a microporous film of a polyamide, such as 8-nylon, 6,6-nylon, etc., a polyethylene, a polypropyrene, polysulfone as is disclosed in Japanese patent application (OPI) No. 21677/78, etc. Further, the reagent layer may comprises a polymer particle-structure as is disclosed in Japanese patent application (OPI) Nos. 101,760/82 and 101,761/82 and a porous material having continuous voids wherein polymer particles, glass particles, diatomaceous earth, etc. are bonded using hydrophilic or non-water absorbing polymer.

The amounts of each component in the aforesaid interacting composition and a reagent can be varied over wide ranges according to the nature of the assay component being measured.

In the case of using a light-transmitting support, the practical construction of the dry-analytical element of this invention are as follows.

(1) An analytical element composed of a support having formed thereon, a reagent layer which may have a further function as a corpuscle filter layer, and a liquid spreading layer.

(2) An analytical element composed of a support having formed thereon, in succession, a detection layer, a reagent layer, and a liquid spreading layer.

(3) An analytical element composed of a support having formed thereon, in succession, a reagent layer, a light reflection layer, and a liquid spreading layer, one of said layers may have a further function as a corpuscle filter layer.

(4) An analytical element composed of a support having formed thereon, in succession, a detection layer, a reagent layer, a light reflection layer, and a liquid spreading layer.

(5) An analytical element composed of a support having formed thereon, in succession, a detection layer, a light reflection layer, a reagent layer, and a liquid spreading layer (said light reflection layer or liquid spreading layer may have a further function as a corpuscle filter layer).

In elements (1) to (3) described above, a water absorbing layer may be formed between the support and the reagent layer.

The water-absorbing layer is a layer which is permeable to water but substantially impermeable to the substance to be finally detected. This layer is provided, preferably between a support and a detecting layer or a reagent layer, in cases where the substance to be finally detected is a sparingly diffusible high polymeric substance. Such a water-absorbing layer preferably comprises a film-forming hydrophilic polymer which is swollen with absorbed water. A preferred embodiment of this invention is aforesaid layer structure (1). When in analytical elements (1) to (3) described above, the liquid spreading layer or the light reflection layer does not have a function as a corpuscle filter layer, a corpuscle filter layer is formed between the reagent layer and the liquid spreading layer. Also, when in analytical elements (3) and (4), the liquid spreading layer or the light reflection layer do not have a function as a corpuscle filter layer, a corpuscle filter layer is formed between the reagent layer and the detection layer or between the liquid spreading layer or the reagent layer and the light reflection layer. Furthermore, when in analysis element (5) described above, the liquid spreading layer or the light reflection layer do not have a function as a corpuscle filter layer, a corpuscle filter layer is formed between the reagent layer and the light reflection layer.

The analytical element of this invention preferably has a layer of substantially filtering off all corpuscles apart from the liquid spreading layer. Examples of such a layer include the porous layers described in Japanese patent application (OPI) Nos. 70163/83, 4959/86, 116258/87, 138756/87, 138757/87 and 138758/87.

The analytical element of this invention may have a light reflection layer and such a light reflection layer can be formed between the reagent layer and the detection layer or between the reagent layer and the liquid spreading layer. Also, the liquid spreading layer or corpuscle filter layer may be provided with a function as a light reflection layer. The light reflection layer has a function of shielding the color of a sample being analyzed when spotted onto the liquid spreading layer and, in particular, the red color of hemoglobin and the yellow color of bilirubin, when measuring the detectable change formed in the reagent layer or in the detection layer by measuring light reflected from the layer, and at the same time a function as a light reflection or a background layer.

It is preferred that the light reflection layer is a water-permeable layer composed of a hydrophilic polymer as binder having dispersed therein light reflective fine particles such as particles of titanium oxide, barium sulfate, etc. As the binder, gelatin, a gelatin derivative, polyacrylamide, etc., are preferred. In the case of using a hardenable polymer such as gelatin, a hardening agent may be added thereto. Also, particles of titanium oxide, etc., may be incorporated into the liquid spreading layer, the reagent layer, the corpuscle filter layer, the detection layer, etc., for giving a function as light reflection to such a layer.

One or more layers of the analytical element of this invention may further contain at least one of various additives such as a surface active agent, a coloring agent solvent, a buffer, a binder, a hardening agent, etc., in an amount known in the field of art. Typical examples of these additives are described in U.S. Pat. Nos. 4,258,011, 3,992,158, 4,042,335, 4,144,306, 4,132,528, 4,050,898, 4,275,152, and Japanese patent application (OPI) No. 299/87.

After spotting a whole blood sample to the analytical element, an incubation (heating) can be applied to the analytical element for quickly and accurately obtaining the test result.

When an assay component exists in the analytical element, the assay component causes an interaction with the interacting composition at a rate based on the concentration of the assay component in the sample. By passing the analytical element through a proper apparatus for detecting the dye, the formation rate of the dye or the amount of dye formed corresponding to the concentration of the assay component is measured. The dye can be detected using a proper spectrophotometer as described, for example, in U.S. Pat. No. 4,584,275.

Then, the invention is explained more practically by the following non-limitting examples.

EXAMPLE 1

On a colorless transparent polyethylene terephthalate (PET) film support of 180 μm in thickness having a subbing layer of gelatin was coated an aqueous gelating solution at a dry thickness of 7 μm and dried to form a water absorbing layer.

Then, after uniformly wetting the surface of the water absorbing layer with water of about 25° C., a micro filter FM 300(cellulose acetate membrane filter having the minimum pore size of 3.0 μm, thickness of 140 μm, and void of about 80%, trade name, made by Fuji Photo Film Co., Ltd.) was laminated thereon and dried to integrate it with the water absorbing layer.

Then, Composition 1 and Composition 2 described below were successively coated on the filter layer at a rate shown below and dried to form a first non-fibrous porous layer of a reagent layer.

| | |
|---|---|
| Composition 1 | |
| Gelatin | 0.64 g/m$^2$ |
| Polyoxyethylene Nonylphenyl Ether (n = 40) | 2.5 g/m$^2$ |
| Trihydroxymethylaminomethane | 0.46 g/m$^2$ |
| Potassium Dihydrogen Phosphate | 0.46 g/m$^2$ |
| L-Aspargic Acid | 2.5 g/m$^2$ |
| Magnesium Chloride (anhydrous) | 0.3 g/m$^2$ |
| Peroxidase | 6,400 U/m$^2$ |
| Flavin Adenine Dinucleotide | 28 mg/m$^2$ |
| Thiamine Pirophosphoric Acid | 118 mg/m$^2$ |
| α-Ketoglutaric Acid | 500 mg/m$^2$ |
| Oxaloacetate Decarboxylase | 12,600 U/m$^2$ |
| Pyruvate Oxidase | 35,000 U/m$^2$ |
| (Aqueous solution having a pH of 7.5) | |
| Composition 2 | |
| Leuco Dye (having the structure shown below) | 1.8 g/m$^2$ |
| Polyoxyethylene Nonylphenyl Ether (n = 40) | 0.6 g/m$^2$ |
| (Ethanol solution) | |

Dye: 2-(3,5-Dimethoxy-4-hydroxyphenyl)-4-phenethyl-5-(4-dimethylaminophenyl-)imidazole.

Then, a Micro Filter FM 300 (trade name, made by Fuji Photo Film Co., Ltd.), which acts as a filter layer to the surface of which was attached starch paste through a dot of 100 mesh (area ratio of about 20%) by a screen printing method in an amount of solid component of 3 g/m$^2$, was laminated thereon and dried to form a 2nd non-fibrous porous layer.

Then, a tricot knitted fabric composed of PET spun yarns of 100 S was stuck onto the 2nd non-fibrous porous layer by the dot sticking method as is described in Japanese patent application (OPI) 138756/77 to form a spreading layer and they were integrated.

Thus, an integrated type multilayer analytical element for determining glutamethoxaloacetate transaminase (GOT) was obtained.

Then, GOT (made by Sigma Co., in the United States) originating from pig, was added to fresh human whole blood (heparin-added blood, hematocrit value 44%) to provide four kinds of blood samples of 22 IU/l, 400 IU/l, 800 IU/l, and 1600 IU/l in GOT activity.

The analytical element prepared above was cut into a square piece of 1.5 cm×1.5 cm, inserted in a plastic mount, and each of the aforesaid 4 kinds of blood samples was spotted to each cut element. Thereafter, the reaction was performed at 37° C., and the absorption of 640 n.m. was measured by the reflection light from the side of the PET support after 2.5 minutes and 4 minutes, then, the GOT activity value was calculated using the value calculated as ODt (transmission optical density) by the principle of *Clinical Chemistry,* Vol. 24, 1335(1978). The results obtained are shown in Table 1.

TABLE 1

| Sample No. | GOT Value of Blood | Measured GOT Value |
|---|---|---|
| 1 | 22 IU/l | 21 IU/l |
| 2 | 400 IU/l | 423 IU/l |
| 3 | 800 IU/l | 846 IU/l |
| 4 | 1600 IU/l | 1530 IU/l |

As is apparent from the Table 1, measured GOT values of a standard solution (GOT-added blood) are identical to calculated GOT activity values.

REFERENCE EXAMPLE

Using the same Composition 1 in Example 1 except that peroxydase, oxaloacetate decarboxylase, and pilvinate oxydase were removed, a reference element which did not respond to GOT was prepared.

To the reference element was spotted Blood Sample No. 1 shown above and after allowing to stand 4 minutes at 37° C., the reflection optical density at 640 n.m. was measured from the PET support side. The same measurement was also applied to the analytical element of this invention in Example 1. Also, the same measurement as above was performed by spotting serum to the reference element. The results obtained are shown in Table 2.

TABLE 2

| Analytical Element | Sample | Optical Density |
|---|---|---|
| Reference Element | Serum | 0.16 |
| | Blood No. 1 | 0.15 |
| Element of Example 1 | Blood No. 1 | 0.41 |

From the results shown in Table 2, it can be seen that the presence of blood corpuscles does not give a significant difference in the optical density of the background. Further, the analytical element of this invention in Example 1 gives sufficiently high optical density over the background.

EXAMPLE 2

Support and Reagent Layer

On a colorless transparent polyethylene terephthalate (PET) film support of 180 μm in thickness having a subbing layer of gelatin was coated an aqueous solution of Composition 3 shown below at a dry thickness of 7 μm and dried to form a reagent layer.

| Composition 3 | |
|---|---|
| Deionized Gelatin | 14.2 g/m$^2$ |
| Polyoxyethylene Nonylphenyl Ether (n = 40) | 410 mg/m$^2$ |
| Peroxydase | 6,500 U/m$^2$ |
| Flavin Adenine Dinucleotide | 22 mg/m$^2$ |
| Thiaminepyrophosphoric Acid | 93 mg/m$^2$ |
| Pyruvate Oxidase | 12,300 U/m$^2$ |
| Leuco Dye (having the structure shown below) | 280 mg/m$^2$ |
| Bis[(vinylsulfonylmethylcarbonyl)-amino]methane | 180 mg/m$^2$ |
| pH adjusted to 6.8 | |

Dye 2-(3,5-Dimethoxy-4-hydroxyphenyl)-4-phenethyl-5-(4-dimethylaminophenyl)imidazole.

Then Composition 4 and Composition 5 shown below were coated, in succession, on the reagent layer at the ratio shown below and dried to form a light reflection layer and an adhesive layer.

Liqht Reflection Layer

The light reflection layer was formed by coating an aqueous dispersion of the following composition on the coloring reagent layer and drying.

| Composition 4 | |
|---|---|
| Alkali-treated Gelatin | 3.2 g/m$^2$ |
| Rutile Type Titanium Dioxide Fine Particles | 8.9 g/m$^2$ |
| Polyoxyethylene Nonylphenyl Ether (containing 40 mean oxyethylene units) | 0.5 g/m$^2$ |

Adhesive Layer

The adhesive layer was formed by coating an aqueous solution of the following composition on the light reflection layer and drying.

| Composition 5 | |
|---|---|
| Alkali-treated Gelatin | 3.1 g/m$^2$ |
| Polyoxyethylene Nonylphenyl Ether (containing 40 mean oxyethylene units) | 0.15 g/m$^2$ |

Liquid Spreadinq Layer

After almost uniformly wetting the surface of the aforesaid adhesive layer with water of about 25° C., a tricot knitted fabric of about 250 μm in thickness composed of PET spun yarns of 100 S was placed on the adhesive layer and stuck thereto to be integrated. Then, an aqueous solution of Composition 6 shown below was coated on the liquid spreading layer and dried to provide, thus, a multilayer analytical film for determining GOT.

| Composition 6 | |
|---|---|
| Polyoxyethylene Nonylphenyl Ether (containing 40 mean oxyethylene units) | 1.2 g/m$^2$ |
| Trishydroxymethylaminomethane | 0.3 g/m$^2$ |
| Potassium Dihydrogen Phosphate | 0.36 g/m$^2$ |
| L-Aspargic Acid | 1.92 g/m$^2$ |
| α-Ketoglutaric Acid | 0.32 g/m$^2$ |
| Magnesium Chloride (anhydrous) | 18.7 g/m$^2$ |
| Oxaloacetate Decarboxylase | 12,600 U/m$^2$ |
| Hydroxypropylmethyl Cellulose | 3.2 g/m$^2$ |
| pH adjusted to 7.5 with diluted sodium hydroxide solution. | |

Analytical Slide

The aforesaid analytical film prepared was cut into a square piece of 1.5 cm×1.5 cm and each piece was inserted in a plastic mount to provide an analytical slide for determining GOT activity.

Measurement of GOT Activity

Then, GOT (made by Sigma Co. in the United States) originating from pig, was added to fresh human whole blood (heparin-added blood, hemacrit value 44%) to provide 4 kinds of blood samples of 25 IU/l, 400 IU/l, 800 IU/l and 1580 IU/l in GOT activity.

Each of the 4 kinds of blood samples was spotted on each analytical slide for GOT determination prepared above. Thereafter, the reaction was performed at 37° C., and the absorption of 640 n.m. was measured by reflection from the PET support side after 2.5 minutes and 4 minutes. Then, the GOT activity value was calculated using the value converted into ODt (transmission optical density) by the principle of *Clinical Chemistry*, Vol. 24, 1335(1978). The results obtained are shown in Table 3.

TABLE 3

| Sample No. | GOT Value of Blood | Measured value in the Example |
|---|---|---|
| 5 | 25 IU/l | 23 IU/l |
| 6 | 400 IU/l | 404 IU/l |
| 7 | 800 IU/l | 851 IU/l |
| 8 | 1580 IU/l | 1568 IU/l |

Comparison Examples

By following the same procedure as in Example 2 except that peroxydase and pyruvate oxidase were removed from Composition 3 and Oxaloacetate decarboxylase was removed from Composition 6, a reference element which did not respond to GOT was prepared.

To the element was spotted each of Blood Sample No. 5 and the serum thereof and after allowing the slides to incubate for 4 minutes at 37° C., the reflection optical density at 640 n.m. was measured from the PET support side. The same measurement as above was also performed on the analytical element in Example 2. The results obtained are shown in Table 4.

TABLE 4

| Analytical Element | Sample | Optical Density |
|---|---|---|
| Reference Element | Serum | 0.23 |
| | Blood No. 5 | 0.22 |
| Element of Example 2 | Blood No. 5 | 0.47 |

From the results shown in Table 3, it can be seen that the existence of corpuscles does not give a significant difference in the optical density of the background. Further, the analytical element of this invention shows a sufficiently high optical density over the background.

While the invention has been described in detail and with reference to specific embodiments thereof, it will be apparent to one skilled in the art that various changes and modification can be made therein without departing from the spirit and scope thereof.

What is claimed is:

1. A multilayer analytical element for assay of a component in whole blood sample comprising at least two water-permeable layers, wherein one layer is a sample spreading layer and the other layer is a reagent layer, wherein one layer or more of said water-permeable layers contain a composition which interacts with said component in whole blood sample, wherein the composition forms a dye capable of being detected by a spectrophotometry at a wavelength of 600 n.m. or longer, when the composition interacts with said component in whole blood sample.

2. The multilayer analytical element as claimed in claim 1, wherein said water-permeable layers containing said composition is the sample spreading layer, the reagent layer, or the sample spreading layer and the reagent layer.

3. The multilayer analytical element as claimed in claim 1, wherein the outermost layer is a liquid spreading layer.

4. The multilayer analytical element as claimed in claim 1, wherein the element further comprises a light reflection layer between the water spreading layer and the reagent layer.

5. The multilayer analytical element as claimed in claim 1, wherein said reagent layer contains at least a component of the composition, said component of the composition being able to form said dye, and said element further comprises a corpuscle filter layer between the sample spreading layer and the reagent layer.

6. The multilayer analytical element as claimed in claim 1, wherein said reagent layer contains at least a component of the composition, said component of the composition being able to form said dye, and the sample spreading layer functions also as a corpuscle filter layer.

7. The multilayer analytical element as claimed in claim 1, wherein said reagent layer contains at least a component of the composition, said component being able to form the said dye, and said element further comprises a light reflection layer between the liquid spreading layer and the reagent layer.

8. The multilayer analytical element as claimed in claim 6, wherein the reagent layer contains the entire composition.

* * * * *